(12) United States Patent
Willard

(10) Patent No.: US 9,844,409 B2
(45) Date of Patent: *Dec. 19, 2017

(54) OSTIAL RENAL NERVE ABLATION

(71) Applicant: Boston Scientific Scimed, Inc., Maple Grove, MN (US)

(72) Inventor: Martin R. Willard, Burnsville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/212,034

(22) Filed: Jul. 15, 2016

(65) Prior Publication Data

US 2016/0324574 A1 Nov. 10, 2016

Related U.S. Application Data

(63) Continuation of application No. 14/617,204, filed on Feb. 9, 2015, now Pat. No. 9,414,885, which is a (Continued)

(51) Int. Cl.
| | |
|---|---|
| *A61B 18/18* | (2006.01) |
| *A61B 18/14* | (2006.01) |
| *A61N 7/02* | (2006.01) |
| *A61B 18/08* | (2006.01) |
| *A61B 18/00* | (2006.01) |
| *A61N 7/00* | (2006.01) |

(52) U.S. Cl.
CPC ........ *A61B 18/1492* (2013.01); *A61B 18/082* (2013.01); *A61N 7/022* (2013.01); *A61B 2018/0022* (2013.01); *A61B 2018/00267* (2013.01); *A61B 2018/00375* (2013.01); *A61B 2018/00404* (2013.01); *A61B 2018/00434* (2013.01); *A61B 2018/00511* (2013.01); *A61B 2018/00577* (2013.01); *A61N 2007/003* (2013.01); *F04C 2270/041* (2013.01)

(58) Field of Classification Search
CPC .............. A61B 18/082; A61B 18/1492; A61B 2018/0022; A61B 2018/00267; A61B 2018/00375; A61B 2018/00404; A61B 2018/00434; A61B 2018/00511; A61B 2018/00577; A61N 2007/003; A61N 7/022; F04C 2270/041

See application file for complete search history.

(56) References Cited

U.S. PATENT DOCUMENTS

| | | | | |
|---|---|---|---|---|
| 2003/0055422 A1* | 3/2003 | Lesh | ........... | A61B 18/1492 606/41 |
| 2007/0083195 A1* | 4/2007 | Werneth | ........... | A61B 18/1492 606/41 |

* cited by examiner

*Primary Examiner* — George Manuel

(57) ABSTRACT

A catheter including an elongated shaft having a distal end and a proximal end, where the catheter includes a thermal element at the distal end thereof. The thermal element may be used in an ablation procedure or other procedure to heat a tissue adjacent a vessel. In some instances, the thermal element may be positioned in a first vessel and may operate to heat tissue adjacent a second vessel or adjacent an ostium between the first vessel and the second vessel. Further, the catheter may include an expandable portion on which the thermal element may be connected or positioned. The expandable portion(s) may comprise a basket or cage, a balloon, a memory shape and formable portion, and/or to other mechanical expanders.

20 Claims, 16 Drawing Sheets

Related U.S. Application Data continuation of application No. 13/671,244, filed on Nov. 7, 2012, now Pat. No. 8,951,251.

(60) Provisional application No. 61/557,239, filed on Nov. 8, 2011.

OSTIAL RENAL NERVE ABLATION

CROSS-REFERENCE TO RELATED APPLICATION

This application is a continuation of U.S. patent application Ser. No. 14/617,204, filed on Feb. 9, 2015, which is a continuation of U.S. patent application Ser. No. 13/671,244, filed on Nov. 7, 2012, now U.S. Pat. No. 8,951,251, which claims the benefit of U.S. Provisional Application Ser. No. 61/557,239, filed Nov. 8, 2011, the entire disclosures of which are incorporated herein by reference.

TECHNICAL FIELD

The disclosure is directed to devices for insertion into bodily vessels. More particularly, the disclosure is directed to devices for use in tissue ablation procedures.

BACKGROUND

Conventional catheters and similar devices are used in medical procedures to gain access to interior regions of bodies. An illustrative region of a body in which catheters are often used is in the cardiovascular system. Typically, a catheter for insertion into a body may have a distal end for insertion into an interior of the body and a proximal end that remains exterior to the body. Catheters may be used in a variety of medical procedures including, but not limited to, ablation procedures, angioplasty procedures, therapeutic procedures, diagnostic procedures and exploratory procedures, among others.

SUMMARY

The disclosure is directed to several alternative or complementary designs, materials and methods of using medical device structures and assemblies. Although it is noted that conventional catheters and similar devices exist, there exists a need for improvement on those devices.

Accordingly, one illustrative embodiment of the disclosure may include a catheter having an elongated shaft with a distal end and a proximal end at opposing ends thereof. The distal end of the elongated shaft may include a thermal element positionable in a lumen of a first vessel that may be used for heating and/or ablating tissue adjacent a second vessel and/or an ostium between the first vessel and second vessel and/or other tissue through the use of an energy field emitted from the thermal element or through the use of another technique. In addition, the distal end of the catheter may be configured to expand to facilitate placing thermal elements near target areas in the first vessel and heating perivascular tissue adjacent the second vessel and/or the ostium between the first vessel and the second vessel and/or other tissue. Illustrative examples of an expandable portion of the catheter may include a cage, a balloon, a memory shape and formable portion, and other expandable features configured to include at least one thermal element thereon. In the examples, the catheter may include a sheath having a lumen through which the elongated shaft is inserted, where the sheath may facilitate positioning the expandable feature(s) in a first position when it is covering the expandable feature(s) and facilitate positioning the expandable features in a second position when the sheath is retracted. Further, illustrative examples of the catheter may include a guide wire and activation or electrically conductive wires connected to the thermal elements, where the thermal elements receive power from the activation wire(s) to which they are connected and the guide wire may be configured to be extended into the second vessel to receive conveyed thermal energy from the thermal element to ablate, modify or destroy perivascular tissue about the second vessel and/or the ostium between the first vessel and the second vessel and/or other tissue.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which.

Figure 1:
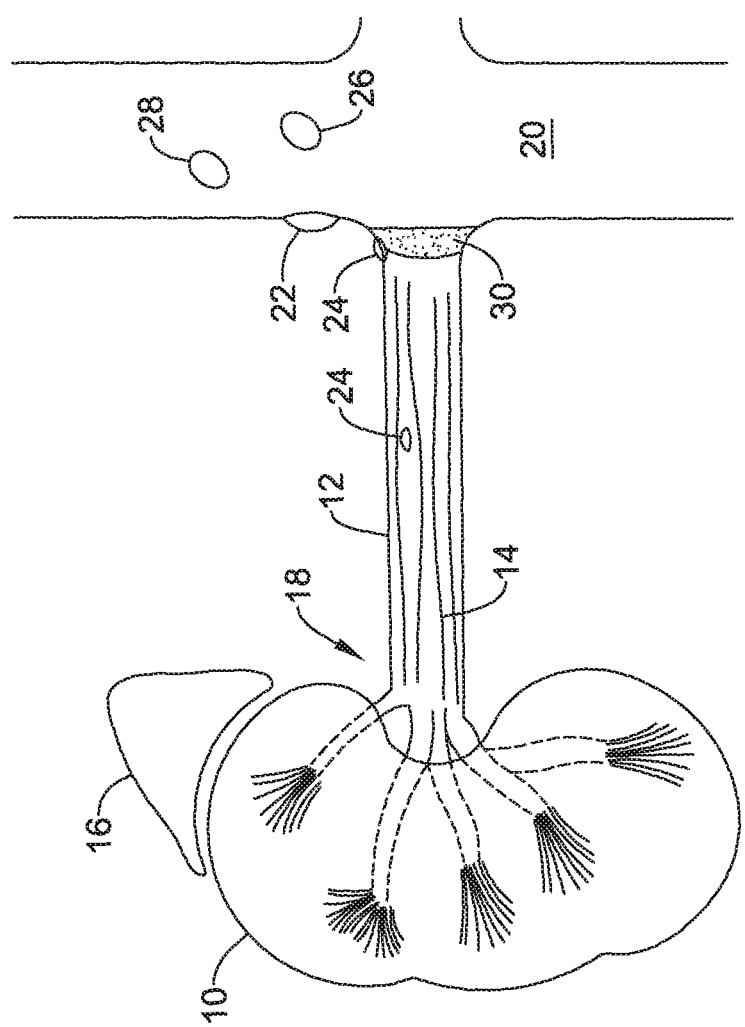
FIG. 1 is a schematic view of a right kidney and renal vasculature extending from an abdominal aorta.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

FIG. 1 is an example illustration of a kidney 10 and renal vasculature including a renal artery 12 branching laterally from an abdominal aorta 20. Generally, the left and right kidneys are supplied with blood from respective right and left lateral surfaces of the abdominal aorta 20. Each of the right and left renal arteries extend from the abdominal aorta 20 to respective renal sinuses proximate the hilum 18 of the kidneys, and branch into segmental arteries and into arteries within the kidney 10. Typically, the renal arteries and the kidneys receive about 20% of total cardiac output which, for a typical person, represents about 1200 mL of blood flow through the kidneys per minute.

Also shown in FIG. 1 is a right suprarenal gland 16, which may be commonly to referred to as a right adrenal gland. The suprarenal gland 16 is usually a star-shaped endocrine gland that rests on top of kidney 10. The primary function of the suprarenal glands may be to regulate a stress response of a body through synthesis of corticosteroids and catecholamines, including cortisol and adrenaline (epinephrine), respectively. Encompassing the kidneys 10, suprarenal glands 16, renal vessels 12 and adjacent perirenal fat is the renal fascia (not shown), which is a fascial pouch derived from extraperitoneal connective tissue.

The autonomic nervous system of the body controls involuntary actions of the smooth muscles in blood vessels, the digestive system, heart and glands. The autonomic nervous system is divided into the sympathetic nervous system and the parasympathetic nervous system. Generally, the parasympathetic nervous system prepares the body for rest by lowering heart rate, lowering blood pressure and simulating digestion. The sympathetic nervous system may effectuate the body's fight or flight response by increasing heart rate, increasing blood pressure and/or increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 16. This release of adrenaline is triggered by the neurotransmitter acetylcholine released from preganglionic sympathetic nerves.

The kidneys and ureters (not shown) may be innervated by renal nerves 14. FIG. 1 depicts illustrative sympathetic innervations of the renal vasculature, primarily innervations of renal artery 12. Functions of sympathetic innervations of the renal vasculature may include regulation of renal blood flow and pressure, stimulation of rennin release, and direct stimulation of water and sodium ion reabsorption, among other functions.

Most of the nerves 14 innervating the renal vasculature may be sympathetic postganglionic fibers arising from the superior mesenteric ganglion 26. Renal nerves 14 may extend generally axially along the renal arteries 12, enter kidneys 10 at or near the hilum 18, follow branches of renal arteries 12 within kidney 10 and extend to individual nephrons of kidney 10. Other renal ganglia, such as renal ganglia 24, superior mesenteric ganglion 26, the left and right aorticorenal ganglia 22, and celiac ganglia 28 may also innervate the renal vasculature.

A focal point for renal innervations is the ostia 30 (e.g., the dotted area in FIG. 1) between renal arteries 12 and abdominal aorta 20. Generally, postganglionic nerve fibers arising from renal ganglia innervate renal arteries 12 along a path that includes ostia 30.

Sympathetic signals to kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22. The postsynaptic sympathetic signals then travel along nerves 14 of renal artery 12 to kidney 10. Presynaptic parasympathetic signals travel to sites near kidney 10 before they synapse on or near kidney 10.

Renal nerves 14 may innervate smooth muscle of the wall of renal artery 12 and extend lengthwise in a generally axial or longitudinal manner from ostium 30 (e.g., the opening between renal artery 12 and aorta 20 and the portions of the vessel adjacent thereto) along the wall of renal artery 12, as seen in FIG. 1. The smooth muscle of renal artery 12 may be under involuntary control of the autonomic nervous system. An increase in sympathetic activity, for example, tends to contract the smooth muscle, which reduces the diameter of a lumen of renal artery 12 and decreases blood perfusion. A decrease in sympathetic activity tends to cause the smooth muscle to relax, which may result in vessel dilation and an increase in a diameter of the lumen of renal artery 12 and blood perfusion. Conversely, increased parasympathetic activity tends to relax the smooth muscle, while decreased parasympathetic activity tends to cause smooth muscle contraction.

Figure 2:
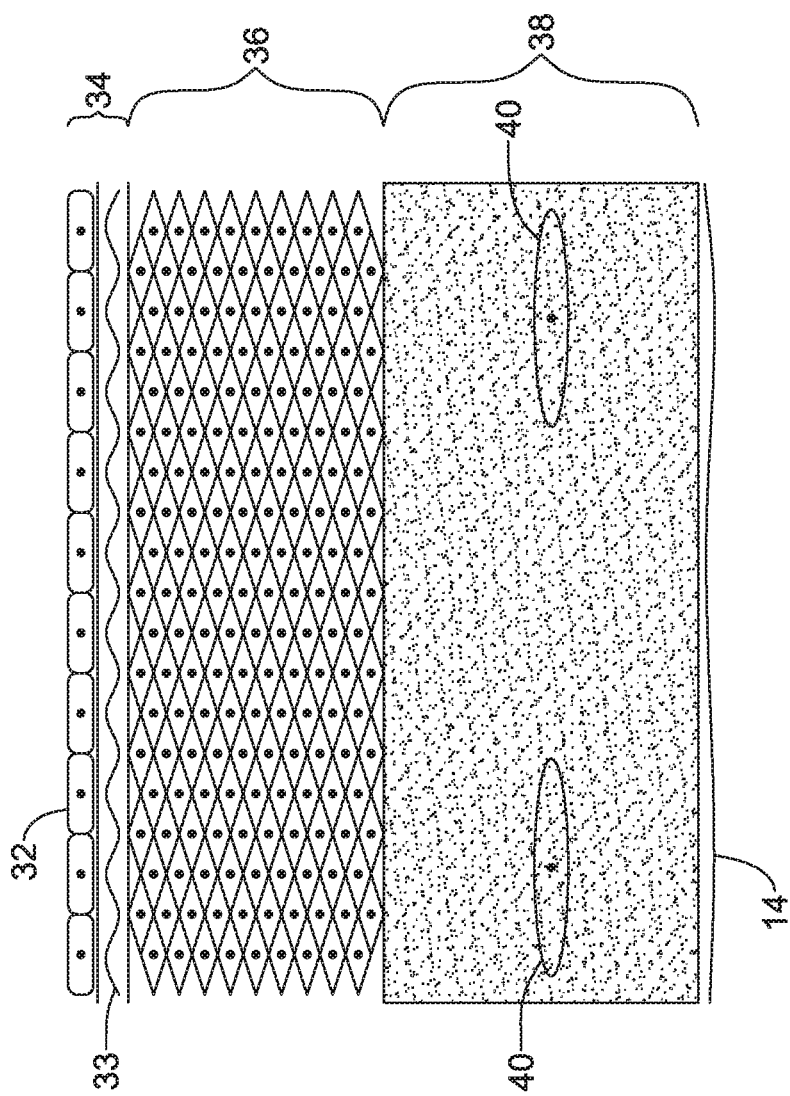
FIG. 2 is a sectional schematic view of tissue layers of a renal artery.

As depicted in FIG. 2, a partial longitudinal cross-section through renal artery 12 shows various tissue layers of the wall of renal artery 12, which includes ostium 30 adjacent renal artery 12. The innermost layer of renal artery 12 comprises endothelium 32, which is the innermost layer of intima 34 and is supported by an internal elastic membrane 33. Endothelium 32 is a single layer of cells that contacts the blood flowing through a lumen of renal artery 12. Endothelium cells are typically polygonal, oval or fusiform and have very distinct round or oval nuclei. Cells of the endothelium 32 are involved in several vascular functions, including control of blood pressure by way of vasoconstriction and vasodilation, blood clotting and acting as a barrier layer between contents within the lumen of renal artery 12 and surrounding tissue, such as the membrane of intima 34 separating intima 34 from media 36 and the adventitia 38. The membrane or maceration 33 of intima 34 is a fine, transparent, colorless structure which is highly elastic and commonly has a longitudinal corrugated pattern.

Adjacent the intima 34 is the media 36, which is the middle layer of renal artery 12. Media 36 is made up of smooth muscle and elastic tissue. Media 36 may be readily identified by its color and by the transverse arrangement of its fibers. For example, media 36 may consist principally of bundles of smooth muscle fibers arranged in a thin plate-like manner or lamellae and disposed circularly around a wall of renal artery 12. The outermost layer of renal artery is the adventitia 38, which is made up of connective tissue. Adventitia 38 includes fibroblast cells 40 that play an important role in wound healing. Further, in FIG. 2, a renal nerve 14 is shown proximate adventitia 38, which will eventually pass into renal artery 12 via ostium 30, and extend longitudinally along the wall of renal artery 12. A main trunk of renal nerves 14 generally lies in or on adventitia 38 of renal artery 12, with certain branches coursing into media 36 to innervate the smooth muscle of renal artery 12.

Figure 4:
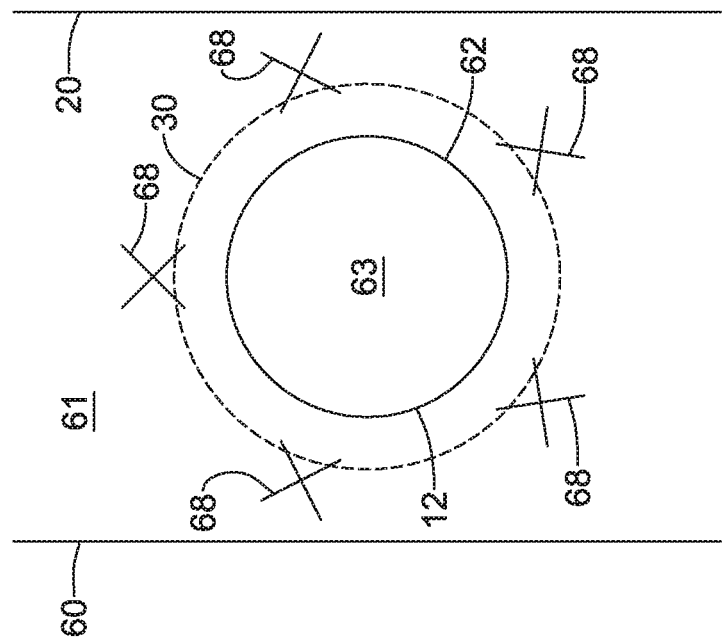
FIG. 4 is a schematic sectional view of FIG. 3, with the catheter apparatus removed, taken along line 4-4 of the first and second vessels according to an aspect of the disclosure.
Figure 3:
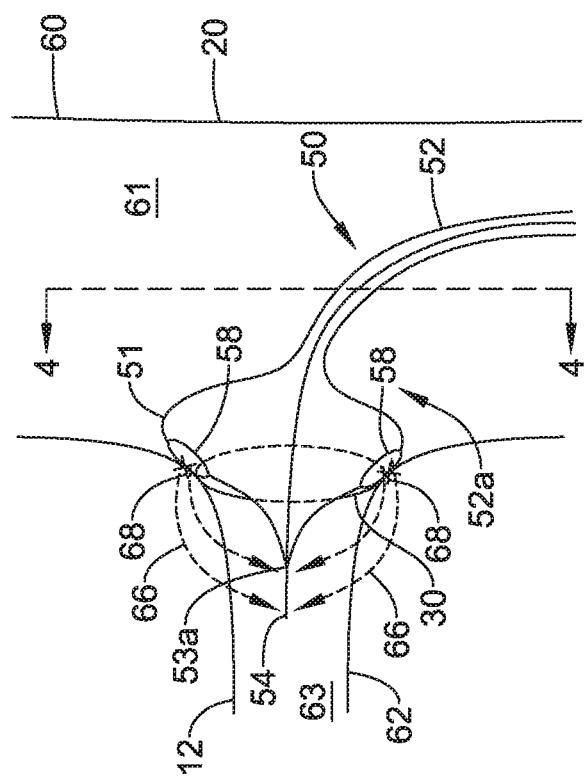
FIG. 3 is a schematic view of a catheter apparatus inserted into a first vessel ablating tissue in a second vessel according to an aspect of the disclosure.

Devices, systems and procedures consistent with the present disclosure may be used on or with the described features of the vascular and nervous systems and may be directed toward delivering thermal energy to ostium 30 and/or an area adjacent ostium 30 associated with renal artery 12 in order to modify, disrupt or terminate renal nerve 14 activity, or to serve another feature consistent with this disclosure. In an illustrative example, as seen in FIGS. 3 and 4, a catheter 50 comprising an elongated member 52 having thermal elements 58 connected thereto and a guide wire 54 extending there through may be inserted into a vascular system and into a lumen 61 of a first vessel 60, for example abdominal aorta 20. The catheter 50 may be positioned such that the thermal elements 58 are located at or proximate the inner wall of the first vessel 60 at or proximate to the ostium 30. Further, in the illustrative example, guide wire 54 may extend through a first terminal end 53a of a distal end 52a of elongated member 52 and into a lumen 63 of a second vessel 62 (an optional step), for example renal artery 12, and may function as a ground wire or may have another function. Thermal elements 58 connected to elongated member 52 at or near an expandable portion or feature 51 of elongated member 52 may send thermal energy 66 through target areas 68 at or near ostium 30 (e.g., the dotted circle in FIG. 4) to guide wire 54 in second vessel 62 to complete a bipolar electrical path and accomplish modifying, disrupting or terminating renal nerve activity or for another similar or different therapeutic effect. Thus, the thermal energy 66 emitted from the thermal elements 58 may be focused to pass through the ganglia 24 proximate the ostium 30, localizing the electrical pathway to the region of the ostium 30.

Alternatively or additionally, thermal element 58 may utilize a unipolar electrical path, such that thermal elements 58 do not utilize guide wire 54 to create a bipolar electrical connection. In a unipolar orientation of thermal elements 58, guide wire 54 may remain in first vessel 60 as it is not needed for the purpose of directing thermal engergy (e.g., radio frequency—"RF", ultrasound energy, etc.) to target areas 68. When thermal element 58 does not utilize guide wire 54 as a ground wire or does not comprise guide wire 54, a ground device exterior to the vascular system may be utilized to assist in directing the flow of energy emitting from thermal element 58, or a different strategically placed ground device may be utilized. For example, a ground or return electrode may be positioned on the exterior of the patient's body in some instances. Generally, thermal elements 58 may be electrodes (e.g., a cylindrical radio-frequency (RF) ablation electrode) or other device that facilitates RF heating or ultrasound heating or other similar or different types of heating using an energy field.

Figure 5A:
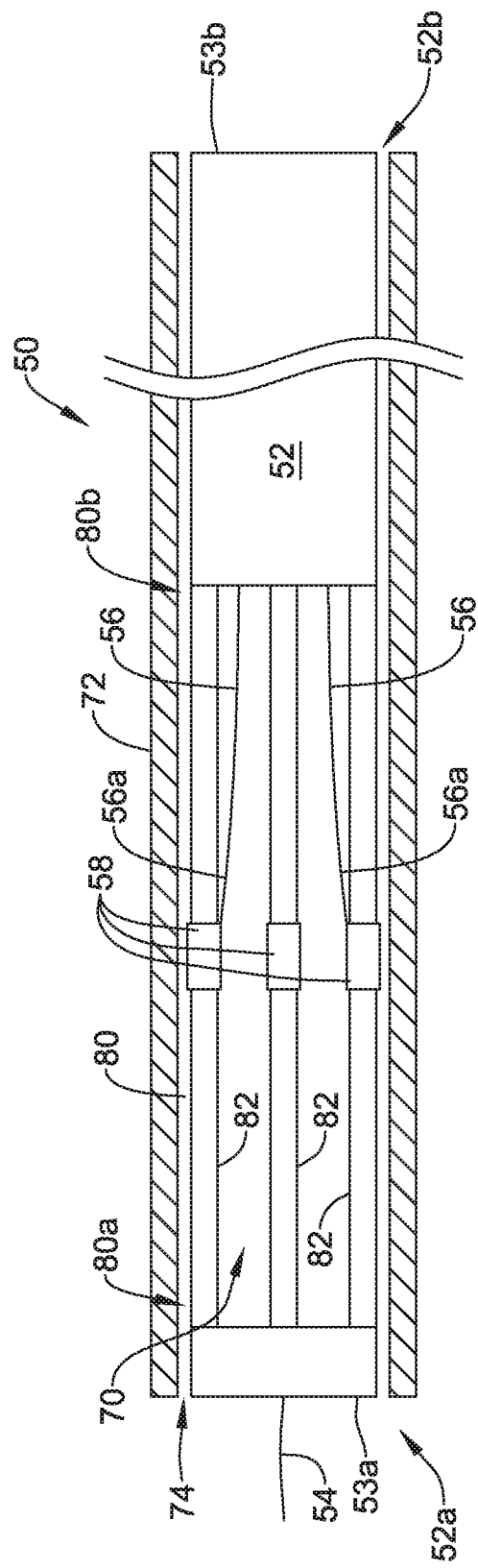
FIG. 5A is a schematic sectional view of a catheter apparatus in a first position according to an aspect of the disclosure.
Figure 5B:
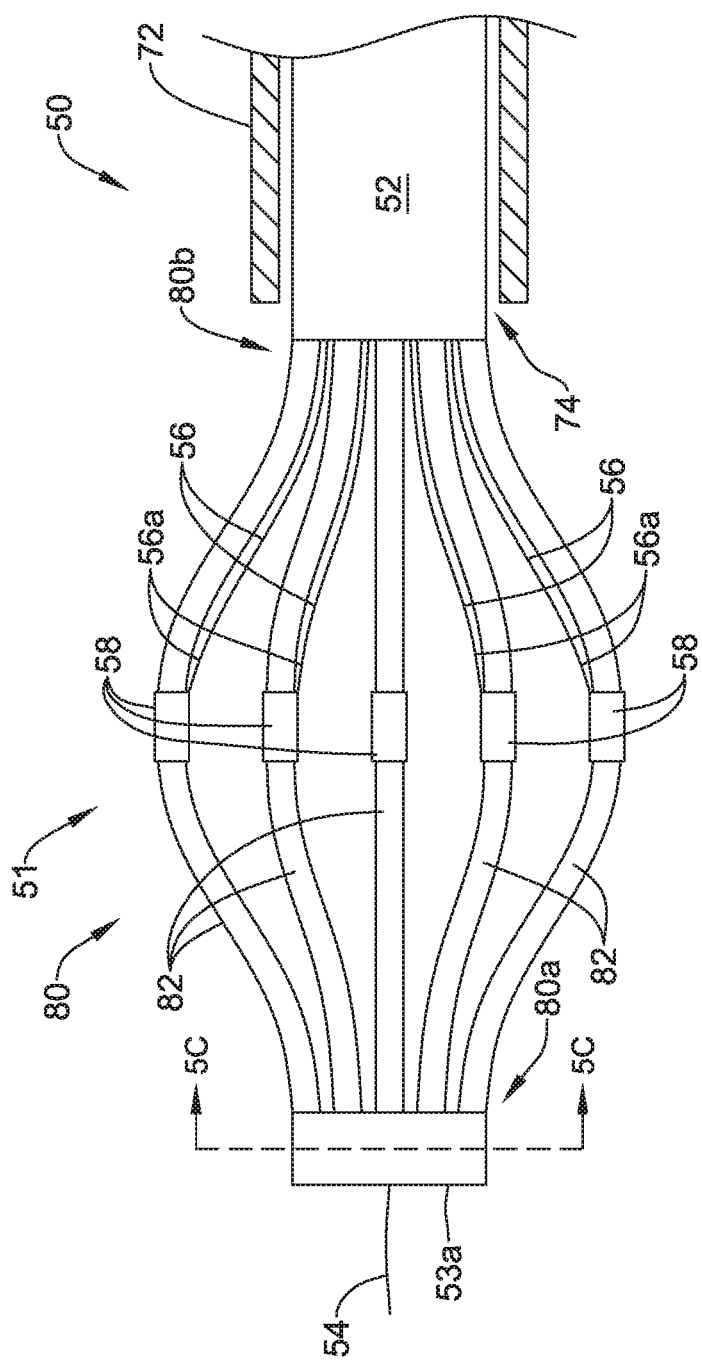
FIG. 5B is a schematic sectional view of the catheter apparatus of FIG. 5A in a second position according to an aspect of the disclosure.
Figure 5C:
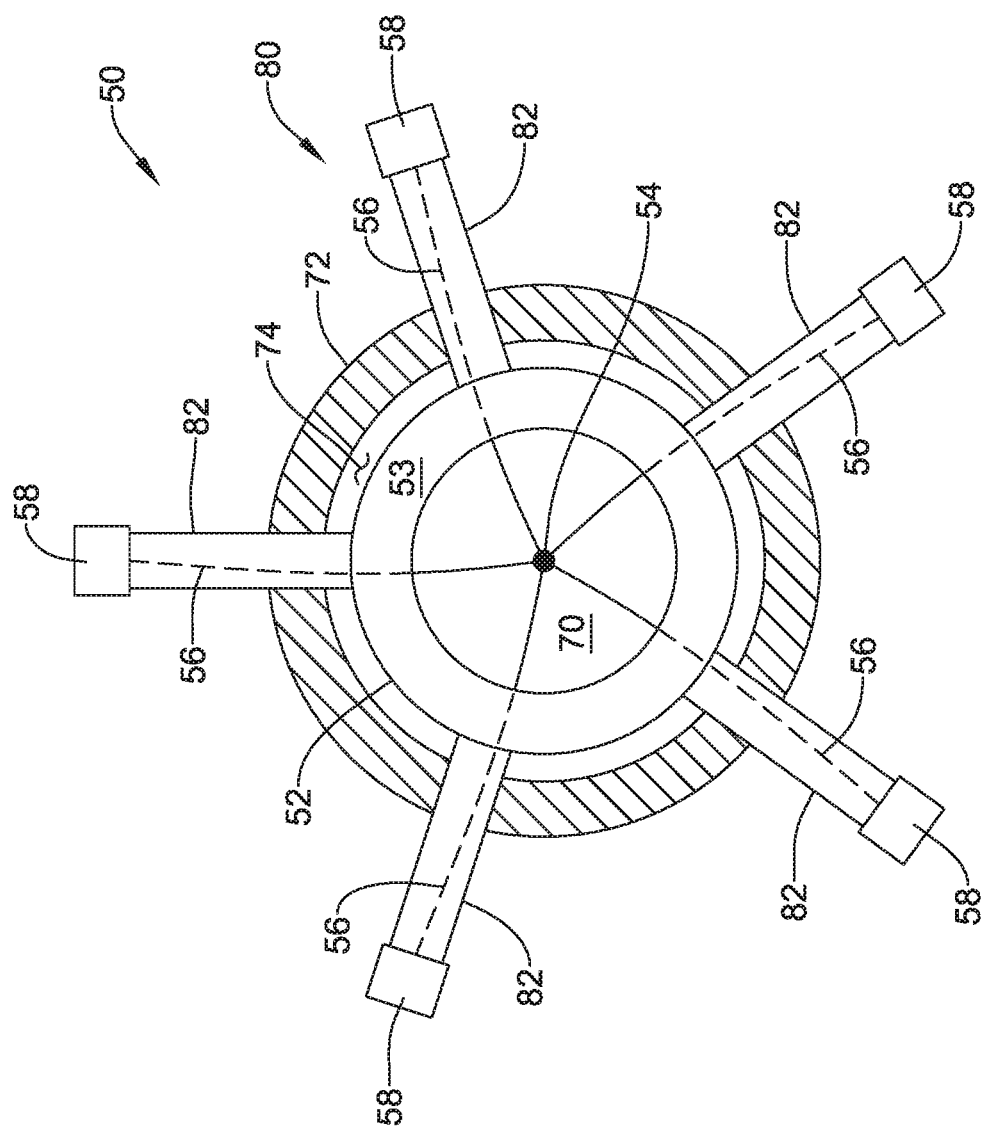
FIG. 5C is a schematic cross-sectional view of the catheter apparatus of FIG. 5B taken along line 5C-5C.
Figure 6A:
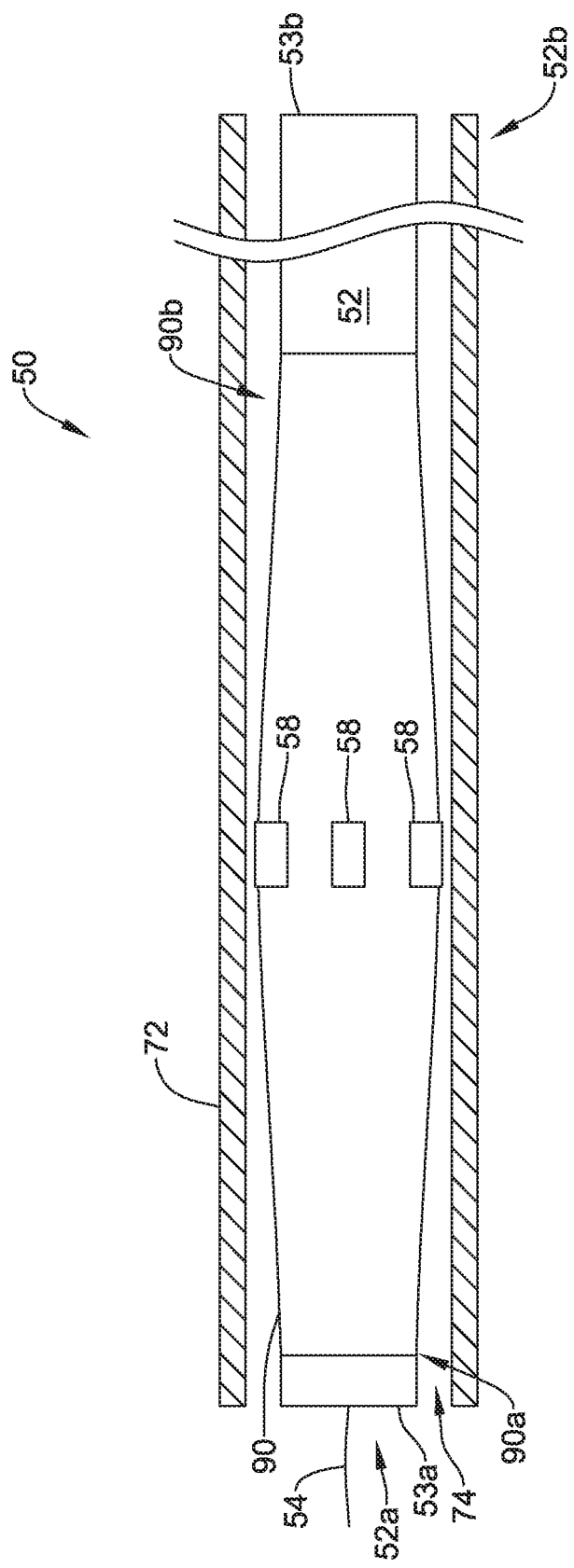
FIG. 6A is a schematic sectional view of a catheter apparatus in a first position according to an aspect of the disclosure.
Figure 8A:
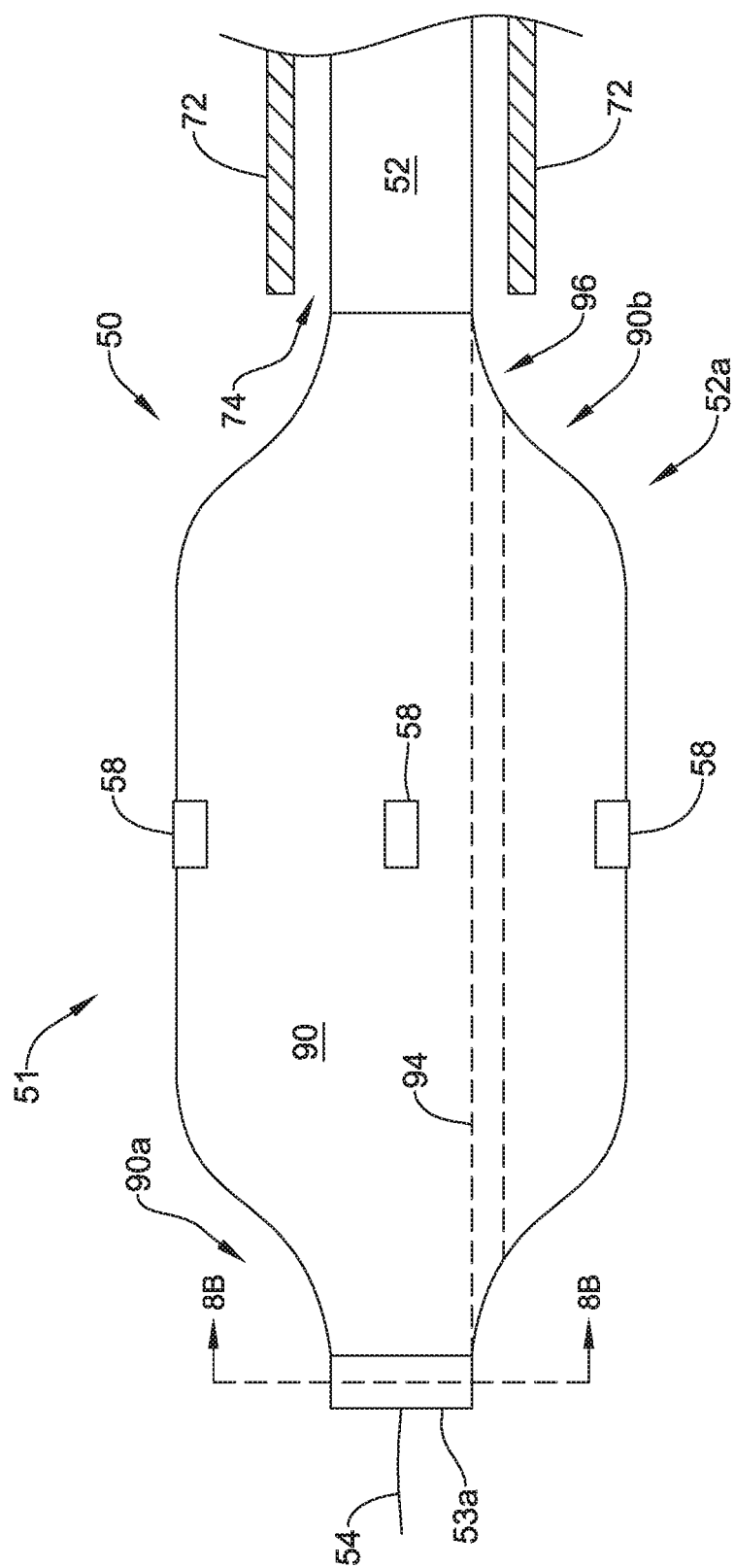
FIG. 8A is a schematic sectional view of a catheter apparatus in a second position according to an aspect of the disclosure.
Figure 8B:
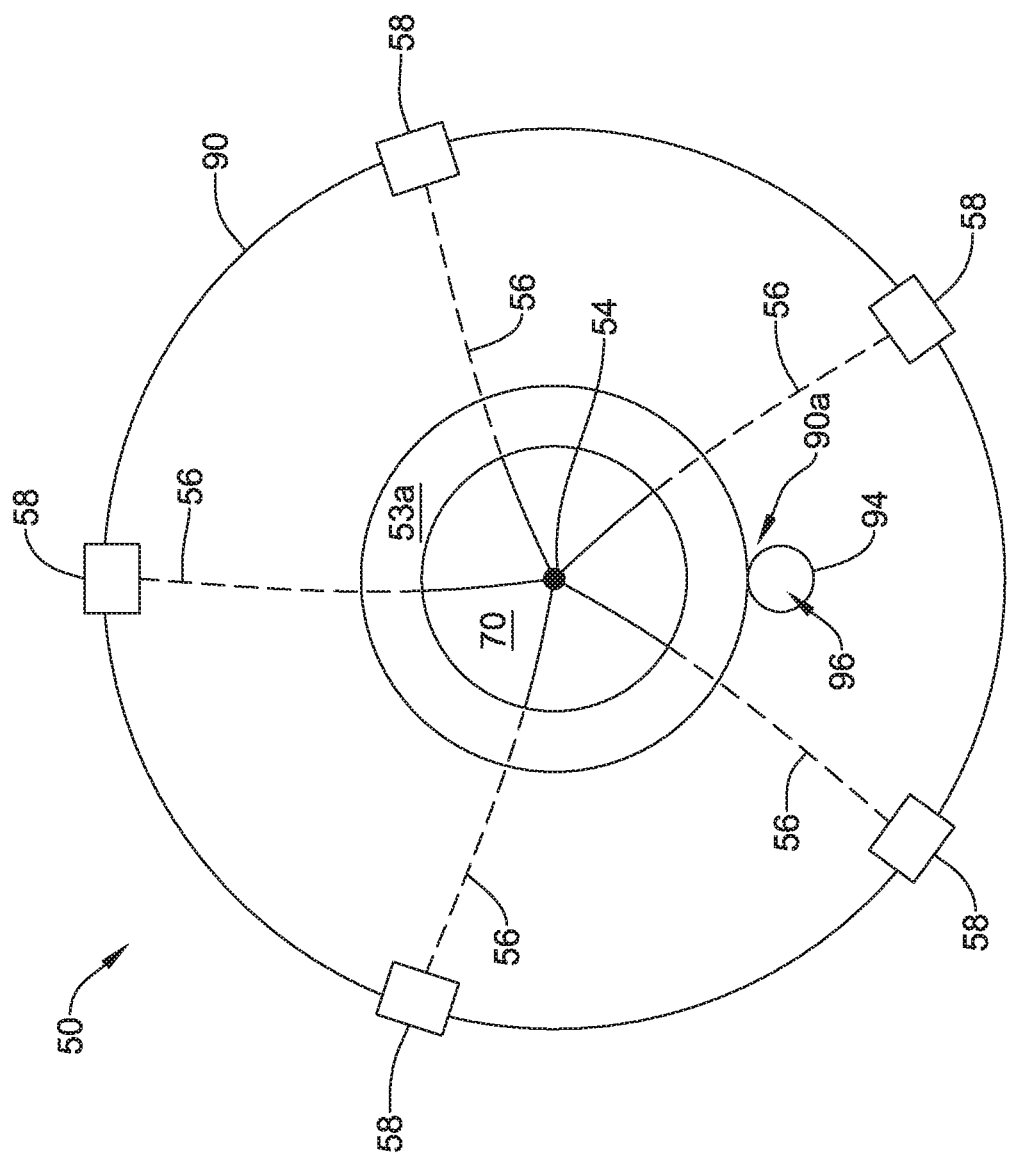
FIG. 8B is a schematic cross-sectional view of the catheter apparatus of FIG. 8A taken along line 8B-8B.
Figure 9A:
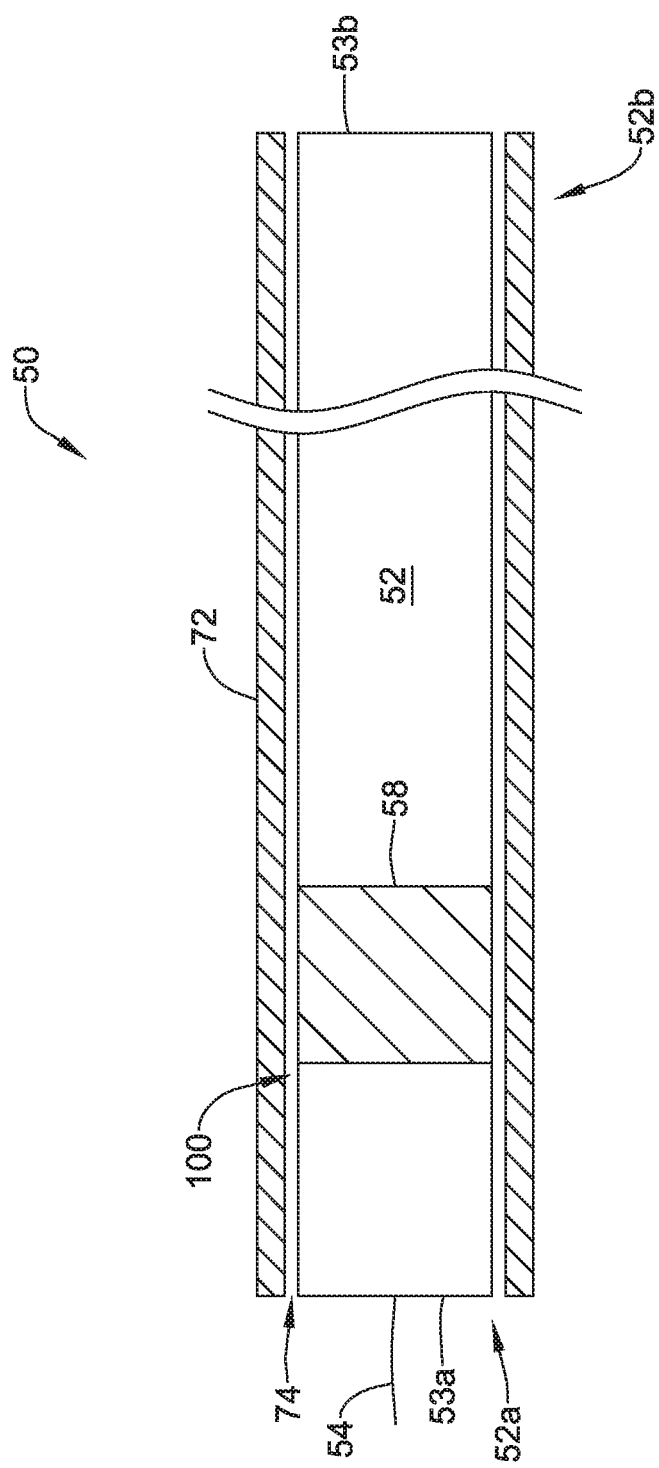
FIG. 9A is a schematic sectional view of a catheter apparatus in a first position according to an aspect of the disclosure.

As seen in FIGS. 5A, 6A and 9A, elongated member or feature 52 of catheter apparatus 50 may have a distal end 52a with a first terminal end 53a and a proximal end 52b with a second a terminal end 53b, where a length of elongated member 52 may be measured from first terminal end 53a to second terminal end 53b. First terminal end 53a may be open to optionally allow guide wire 54 to extend there through and for other purposes. Second terminal end 53b of elongated member 52 may be connected to a handle and/or controller or controlling device (not shown) for controlling movement of distal end 52a and controlling the operation of thermal element(s) 58 attached to distal end 52a, among having other similar and different capabilities. As discussed, catheter 50 may further include guide wire 54 and may further include electrically conductive wires 56 having a distal end 56a and a proximal end (not shown), where wires 54, 56 may extend substantially the length of elongated member 52. To enclose and protect guide wire 54 and one or more electrically conductive or activation wires 56, elongated member 52 may form a lumen 70 through which guide wire 54 and electrically conductive wires 56 may extend. Catheter 50, in addition, may include an outer tubular structure, for example a sheath 72 that may be retractable and/or configured to allow elongated member 52 to retract there through, configured to optionally cover at least a portion of distal end 52a of elongated member 52, as seen in FIGS. 5A-9B. In instances where sheath 72 has been retracted, thermal elements 58 may be configured so as to be exposed and to abut or be placed adjacent to ostium 30 between first vessel 60 and second vessel 62, or near but spaced from the wall of the ostium 30 in the case of an off-the-wall electrode). Additionally, elongated member 52 extending through sheath 72 may be retracted relative to sheath 72, resulting in thermal elements being covered by sheath 72. Sheath 72 may be made of any material. For example, sheath may be made of a polymeric material such as polyamide or polyethylene, or another material.

Distal end 52a of elongated member 52 may include expandable portion(s) or feature(s) 51. Expandable feature 51 may be an expandable cage or basket, a balloon or other mechanical expander. Expandable feature 51 may be configured to mechanically connect to one or more of thermal elements 58 and/or thermal elements 58 may be placed adjacent expandable feature 51. For example, a plurality of thermal elements 58 may be connected to expandable feature 51 and expandable feature 51 may be configured to expand from a first position when elongated member 52 is retracted to a second position, and/or have a modified shape, when sheath 72 is retracted relative to elongated member 52 and/or expandable feature 51. Expandable feature 51 and elongated member 52, generally, may be made out of any material. For example, expandable feature 51 and the rest of elongated member 52 may be made from a polymer, a metal or other similar or different suitable material configured to be inserted into vessels 60, 62 and capable of physical manipulation throughout a vascular system, or another material having similar or different properties.

Power may be supplied to thermal element(s) 58 through its electrical connection with at least one distal end 56a of electrically conductive wires 56. Thus, an operator or controller may control, through signals sent along wires 56 to thermal element(s) 58, when and how energy is emitted from thermal element(s) 58. For example, when thermal elements 58 are connected to expandable feature 51, a controller may choose to power thermal elements 58 when expandable portion is in the second position and may choose to remove power from thermal elements 58 when expandable portion 51 is in the first position.

As seen in FIGS. 5A-5C, expandable portion 51 of elongated member 52 may comprise an expandable basket or an expandable cage 80 positioned at distal end 52a of elongated member 52. Cage 80 may have one or more struts 82 extending at least substantially from a distal end 80a of cage 80 to a proximal end 80b of cage 80. Further, cage 80 may be formed of, for example, a polymeric, electrically nonconductive material, such as polyethylene, polyurethane, polyamide, polyether block amide (PEBA), (i.e., PEBAX™), or other materials including polymeric and metallic materials having shape memory characteristics or another material having similar or different properties. Struts 82 may be equally spaced circumferentially around elongated member 52 and concentric about guide wire 54. Alternatively, struts 82 may be concentrically spaced (or otherwise spaced) from guide wire 54 and separated at any desired interval(s) around elongated member 52, or may take on another configuration. "Concentrically spaced" may be interpreted as a first object (e.g., each strut 82) being an equal distance from a reference second object (e.g., guide wire 54). Separations between adjacent struts 82 and separations between guide wire 54 and struts 82 may allow for fluid (e.g., blood) to flow through cage 80 and cool ablation locations along vessel walls and/or have other functions.

Struts 82 of cage 80 may be configured in the first position, as seen in FIG. 5A, when sheath 72 is covering a substantial portion thereof (e.g., cage 80 is within lumen 74 and elongated member 52 is retracted within sheath 72) and cage 80 and struts 82 may be positioned in the second position, as seen in FIG. 5B, when sheath 72 is substantially retracted with respect to cage 80 and covering non-cage portions of elongated shaft 52. To facilitate the first and second positions, distal end 80a or proximal end 80b of cage 80 may slide on or over and/or relative to a non-cage portion of elongated member 52 and the opposite end of cage 80 may be fixed to a non-cage portion of elongated member 52, or both ends 80a, 80b may be fixed relative to non-cage portions of elongated member 52 or both ends 80a, 80b may slide on or over and/or relative to non-cage portions of elongated member 52. Cage 80 may be manipulated to move from the first position to the second position automatically due to characteristics of the material of cage 80 and/or cage 80 may be manipulated by an operator and/or controller through activation wire(s) 56 or other wires or a wireless communication.

Thermal elements 58 adjacent expandable portion 51 may be positioned on or connected to struts 82 of cage 80. Thermal elements 58 may be positioned on or connected to struts 82 at any position that facilitates thermal elements 58 abutting or being adjacent ostium 30 when sheath 72 is in a retracted position. For example, thermal elements 58 may be placed on or connected to struts 82 such that when struts 82 are in the second position (e.g., expanded position), thermal elements 58 are at or near the largest diameter portion of cage 80, as seen in FIG. 5B, and/or positioned distal of the largest diameter portion of cage 80 when cage 80 is in the second position.

As seen in FIGS. 6A-8B, additionally or alternatively, expandable portion 51 of elongated member 52 may comprise a balloon 90 positioned at distal end 52a of elongated member 52. Balloon 90 may have a distal end (e.g., a first end) 90a and a proximal end (e.g., a second end) 90b, where to facilitate expansion of balloon 90 distal end 90a or proximal end 90b of balloon 90 may slide on or over and/or relative to a non-balloon portion of elongated member 52 and the opposite end of balloon 90 may be fixed to a non-balloon portion of elongated member 52, or both ends 90a, 90b may be fixed relative to non-balloon portions of elongated member 52 or both ends 90a, 90b may slide on or over and/or relative to non-balloon portions of elongated member 52. Such configurations of balloon 90 with respect to non-balloon portions of elongated member 52 may facilitate balloon 90 being situated in the first position (e.g., substantially deflated), as seen in FIG. 6A, when sheath 72 is covering a substantial portion thereof (e.g., when balloon is positioned within lumen 74 and elongated member 52 is retracted) and balloon 90 may be positioned in the second position (inflated), as seen in FIGS. 6B-8B, when sheath 72 is substantially retracted with respect to balloon 90.

Figure 6B:
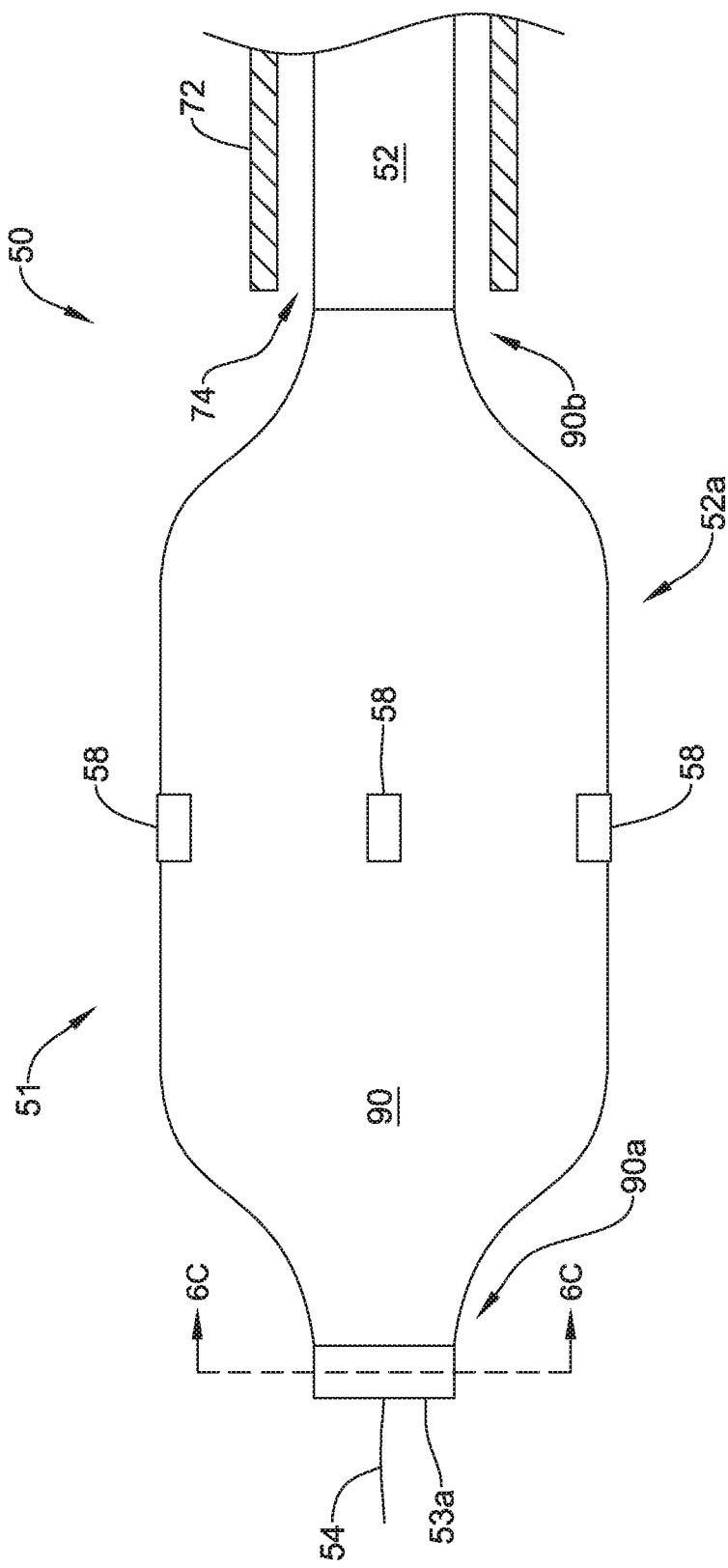
FIG. 6B is a schematic sectional view of the catheter apparatus of FIG. 6A in a second position according to an aspect of the disclosure.
Figure 6C:
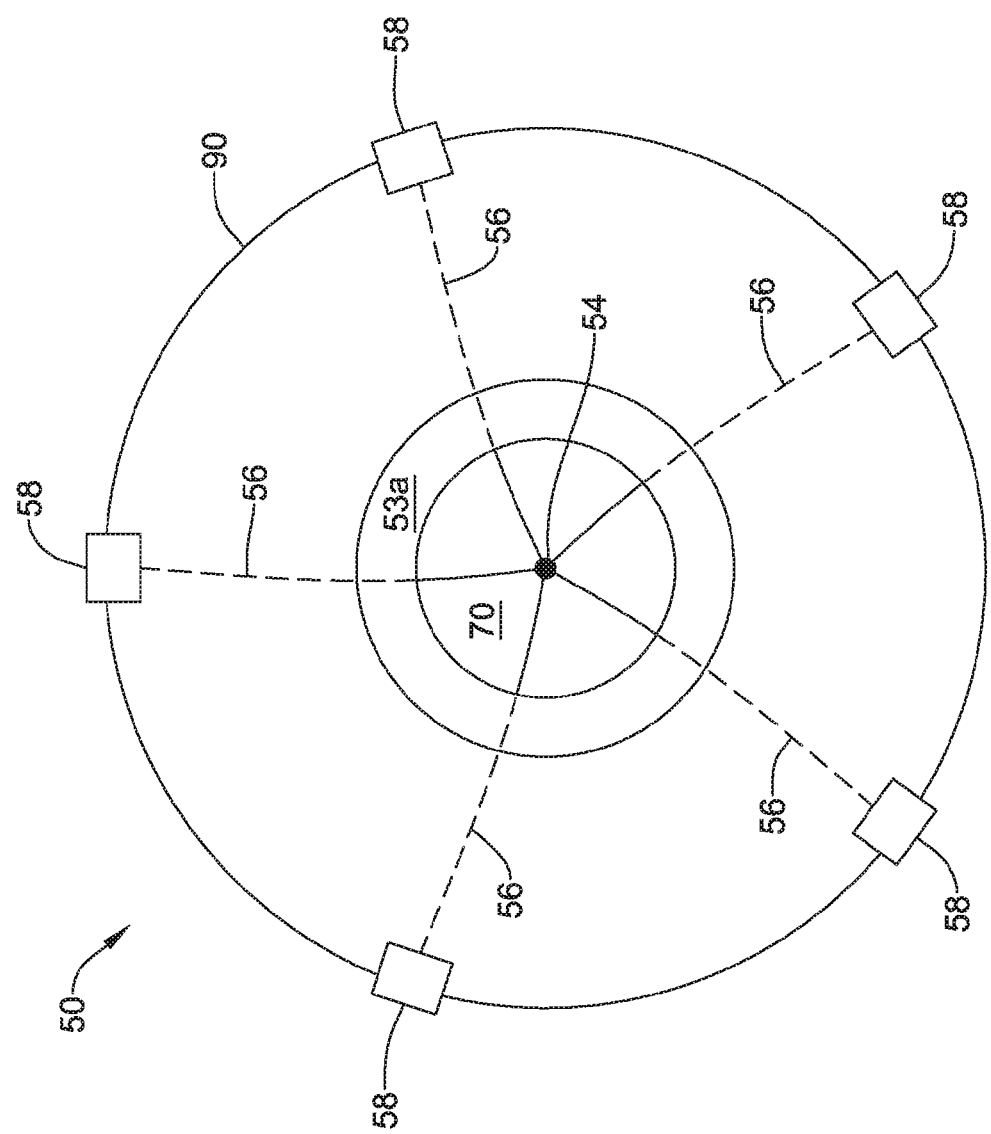
FIG. 6C is a schematic cross-sectional view of the catheter apparatus of FIG. 6B taken along line 6C-6C.
Figure 7A:
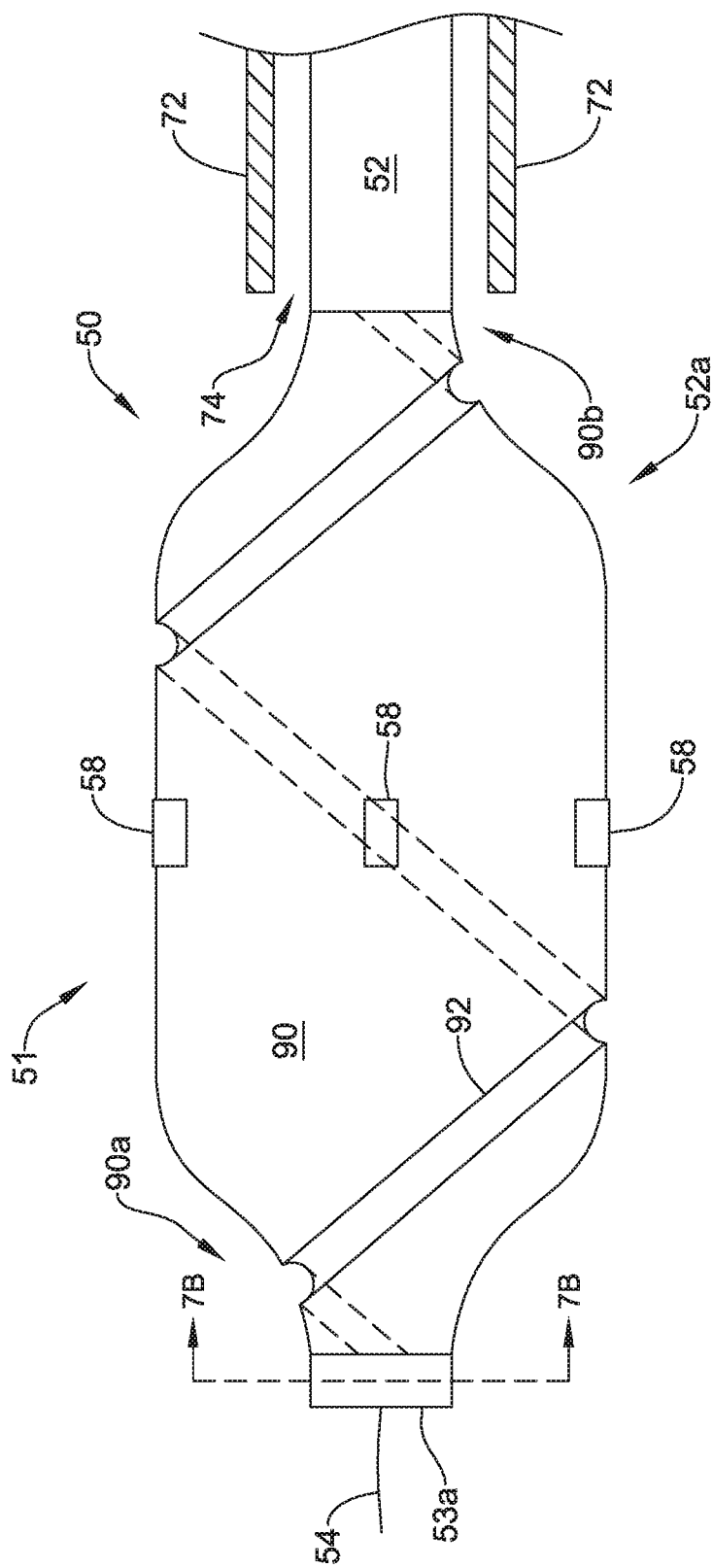
FIG. 7A is a schematic sectional view of a catheter apparatus in a second position according to an aspect of the disclosure.

Thermal elements 58 adjacent expandable feature 51 may be positioned on or connected to balloon 90 at any location. For example, thermal elements 58 may be positioned on or connected to balloon 90 at any position that facilitates thermal elements 58 abutting or being adjacent ostium 30 when sheath 72 is in a retracted position and balloon 90 is in the second position, such that thermal elements 58 may modify, disrupt or terminate functions of perivascular tissue on or near renal artery 12 by sending thermal energy 66 through target areas 68. For example, thermal elements 58 may be placed on or connected to an exterior of balloon 90 such that when balloon 90 is in the second position, thermal elements 58 are at or near the largest diameter portion of balloon 90, as seen in FIGS. 6B, 7A and 8A, and/or positioned distal of the largest diameter portion of balloon 90 in the second position. Alternatively or additionally, thermal elements 58 may be positioned at least partially within balloon 90 or on an interior of balloon 90 or at other positions or other configurations that facilitate directing thermal energy 66 to target areas 68.

Figure 7B:
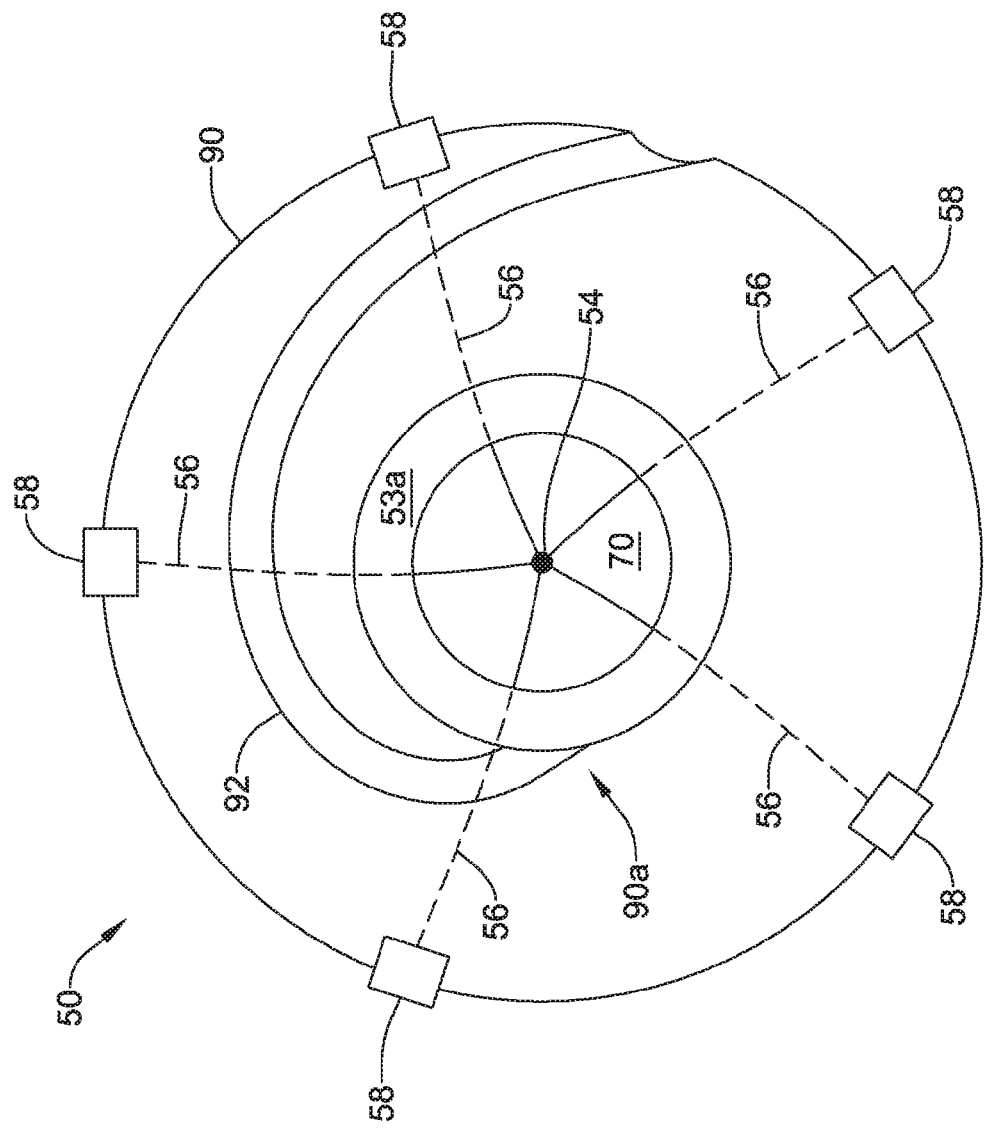
FIG. 7B is a schematic cross-sectional view of the catheter apparatus of FIG. 7A taken along line 7B-7B.

Balloon 90 may be utilized to position thermal elements 58 at or near ostium 30, such that thermal elements 58 may send thermal energy 66 to or through target areas 68, including perivascular tissue. To facilitate the positioning of thermal elements 58, balloon 90 may expand from the first position when balloon is within lumen 74 (e.g., when elongated member 52 is retracted relative to sheath 72) to the second position when sheath 72 is retracted. When balloon 90 is at the expanded second position, as in FIGS. 6B-8B, in first vessel 60, balloon 90 may at least partially block fluid flowing from first vessel 60 to second vessel 62 through ostium 30. To facilitate allowing fluid to flow from first vessel 60 to second vessel 62 while balloon 90 is adjacent ostium 30, balloon 90 may define a helical (or other shaped) flow path 92, as seen in FIGS. 7A and 7B. Helical flow path 92 may extend from proximal end 90b to distal end 90a of balloon 90 allowing fluid to flow from first vessel 60 to second vessel 62 along flow path 92. Flow path 92 may have any configuration; for example, flow path 92 may be a spiral or helical indentation in the outer surface of balloon 90 when it is in the expanded second position, as seen in FIGS. 7A and 7B.

Alternatively or in addition, balloon 90 and/or elongated member 52 may include a flow tube 94 having a lumen 96 extending through balloon 90 from first end 90a (e.g., distal end) to second 90b (proximal end). Lumen 96 of flow tube 94 may be configured to fluidly communicate with first vessel 60 and second vessel 62. For example, flow tube 94 may be positioned within or with respect to balloon 90, as part of catheter 50, to facilitate or create a fluid flow path allowing fluid to flow through lumen 96 from first vessel 60 to second vessel 62 when balloon 90 is in its expanded second position adjacent or near ostium 30.

Figure 9B:
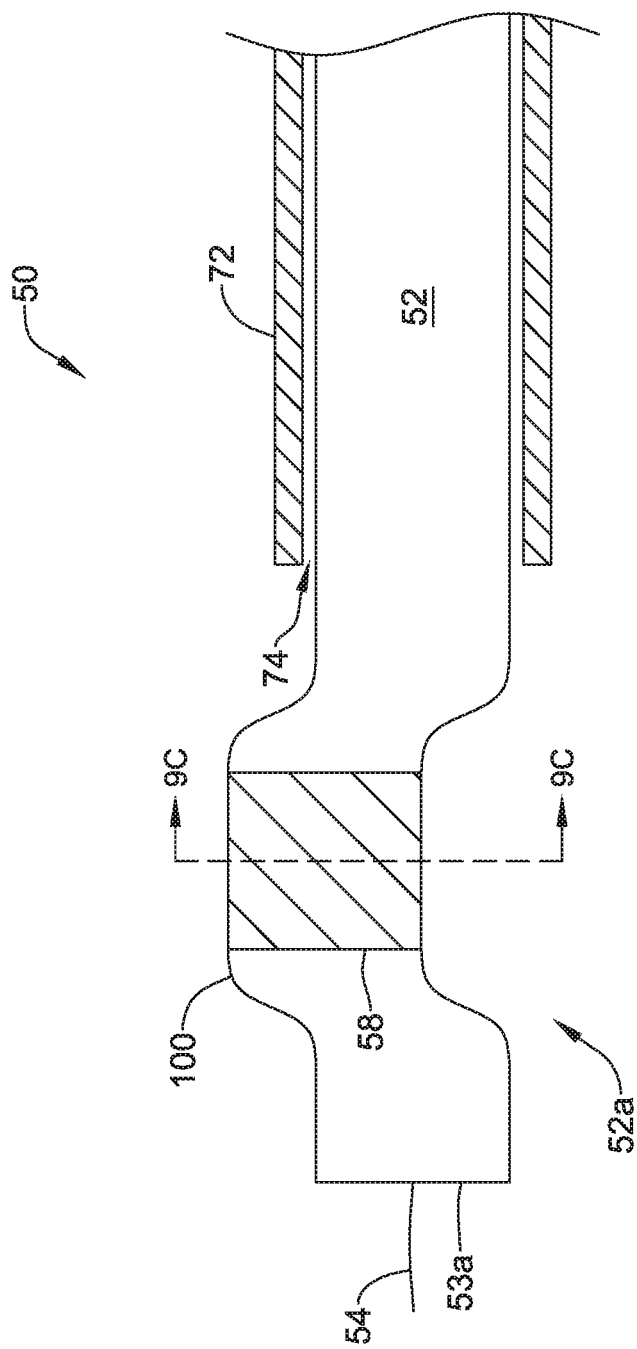
FIG. 9B is a schematic sectional view of the catheter apparatus in FIG. 9A in a second position according to an aspect of the disclosure.
Figure 9C:
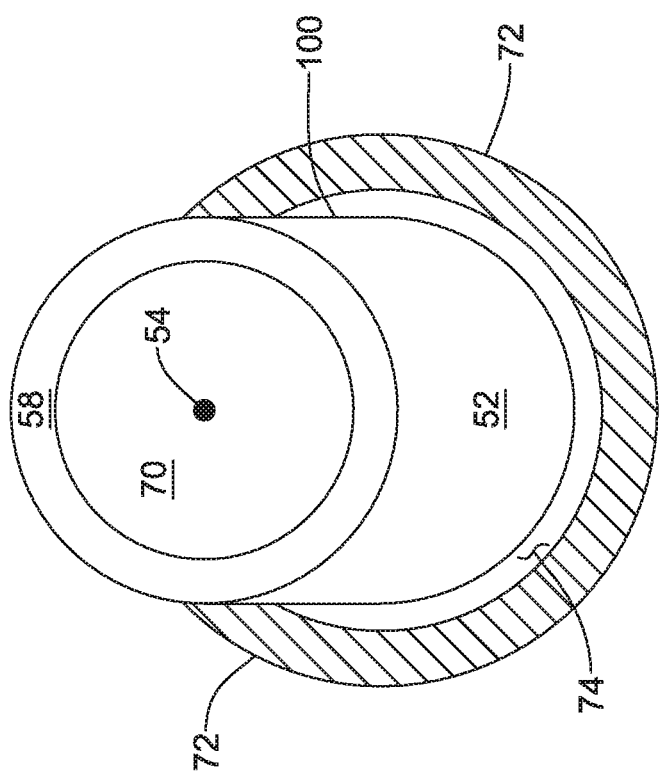
FIG. 9C is a schematic cross-sectional view of the catheter apparatus of FIG. 9B taken along line 9C-9C.

As seen in FIGS. 9A-9C, additionally or alternatively, expandable portion 51 of elongated member 52 may be formed of a shape memory material, such as a shape memory polymer or a shape memory alloy, forming a shape memory and formable portion 100 positioned at a distal end 52a of elongated member 52. When shape memory and formable portion 100 is located within lumen 74 of sheath 72 (e.g., elongated member 52 is retracted into sheath 72), portion 100 may be in the first position, as seen in FIG. 9A, and when sheath 72 is retracted with respect to elongated member 52, portion 100 may at least partially take on a desired shape or configuration of the second position, as seen in FIGS. 9B and 9C. If shape memory and formable portion 100 does not completely take on a desired shape or position of the second position on its own, a controller or operator may be able to facilitate further adjustment of shape memory and formable portion 100 through activation wire(s) 56 or other wires. Alternatively or in addition, shape memory and formable portion 100 may have little, if any, shape memory characteristics and portion 100 may be placed in a desired configuration of the second position substantially entirely by an operator and/or through controller manipulation, where such techniques and required structure may be commonly known in the art. Such configurations of shape memory and formable portion 100 with respect to non-shape-memory or non-formable shape portions of elongated member 52 may facilitate elongated member 52 being situated in the first position, as seen in FIG. 9A, when sheath 72 is covering a substantial portion thereof (e.g., when memory or formable shape portion 100 is positioned substantially within lumen 74 and elongated member 52 is retracted within sheath 72) and memory or formable shape portions 100 may be positioned in the second position, as seen in FIGS. 9B and 9C, when sheath 72 is substantially retracted.

One or more thermal elements 58 positioned adjacent expandable portion 51 may be positioned on or connected to or about memory shape or formable portion 100, as shown in FIGS. 9A-9C. Thermal elements 58 may be positioned on or connected to portion 100 at any position that facilitates thermal elements 58 abutting or being placed adjacent ostium 30 when sheath 72 is in a retracted position and portion 100 is in the second position, such that thermal elements 58 may modify, disrupt or terminate functions of perivascular tissue on or near renal artery 12. For example, thermal elements 58 may be attached to an exterior of portion 100 and configured to be adjacent target areas 68 when portion 100 is in the second position. Alternatively or additionally, thermal elements 58 may be positioned at least partially within memory shape and formable portion 100 or on an interior of portion 100 or at other positions or other configurations that facilitate directing thermal energy 66 from thermal elements 58 to and through target areas 68.

Although expandable portion 51 has been described with respect to basket or cage 80, balloon 90 and portion 100, expandable portion 51 of elongated member 52 may take on various shapes, structures and configurations other than basket or cage 80, balloon 90 and portion 100, as long as the various shapes, structures and configurations may facilitate modifying, disrupting or terminating functions of perivascular tissue adjacent renal artery 12. In addition, although elongated member 52 has been described and depicted as including a single expandable portion, elongated member 52 may comprise more than one expandable portion 51 (e.g., cage 80, balloon 90, etc) at or near distal end 52a or at another location along elongated member 52.

As discussed, catheter 50 may be utilized to ablate, disrupt, modify or destroy perivascular tissue adjacent renal artery 12. A method of or procedure for ablating perivascular tissue may include positioning distal end 52a of elongated shaft 52 in lumen 61 of first vessel 60 of a vascular system, where proximal end 52b may be located substantially exterior to the vascular system. Positioning thermal element(s) 58 adjacent ostium 30 or target areas 68 may include exposing and expanding expandable portion or feature 51 of distal end 52a of elongated shaft 52. To expose and expand expandable portion 51, sheath 72 may be retracted with respect to elongated member 52 and expandable portion 51 may automatically expand after retraction of sheath 72 or expandable portion 51 may be allowed to or forced to expand in response to an operator or controller's signal or direction. For example, when expandable portion 51 is cage 80, expandable portion 51 may begin to expand to its second position automatically when sheath 72 is retracted. Alternatively or in addition, in an illustrative example of when expandable portion 51 is balloon 90, once sheath 72 is at least partially retracted, expandable portion 51 may be begin to expand to its second position after receiving a force at an interior of balloon 90, such as by an inflation fluid delivered to the interior of the balloon 90, that forces balloon 90 to expand. Such a force within balloon 90 may be actuated by a controller and/or operator. Alternatively, balloon 90 may receive a force prior to sheath being retracted, such that expansion of balloon 90 due to the received force automatically retracts sheath 72 with respect to expandable portion 51. Once expandable portion 51 is in the second position, the method or procedure may further include heating the perivascular tissue adjacent second vessel 62 with the use of thermal element(s) 58 in lumen 61 of first vessel 60, where thermal element(s) 58 may emit thermal energy 66 through target area(s) 68, as seen in FIG. 3, or where thermal elements 58 heat the perivascular tissue in another manner.

Once expandable portion 51 has been expanded, or prior thereto, and prior to heating the tissue, expandable portion 51 may be positioned adjacent ostium 30 between first vessel 60 and second vessel 62. When expandable portion 51 has been positioned adjacent ostium 30, thermal elements 58 connected to expandable portion 51 may also be positioned adjacent ostium 30 and target areas 68. At any time before, during or after positioning expandable portion 51 or thermal element(s) 58 adjacent ostium 30, guide wire 54 extending through elongated shaft 52 from proximal end 52b to distal end 52a may be extended through first terminal end 53a and into lumen 63 of second vessel 62.

Once thermal element(s) 58 are positioned adjacent ostium 30 and guide wire 54 is positioned within lumen 63, electrical (e.g., thermal) energy 66 may be conveyed between thermal element(s) 58 in first vessel 60 and guide wire 54 in second vessel 62 to form a bipolar electrical connection. For example, as thermal element 58 may be an ablation electrode and guide wire 54 may be a ground electrode, thermal electrical energy 66 may be directed from thermal element(s) 58 toward guide wire 54 and through vessels 60, 62 and perivascular tissue (e.g., renal nerves 14) to ablate or modify the perivascular tissue or for another purpose. For example, with the thermal elements 58 positioned in the first vessel 60 and/or proximate the ostium 30, the electrical energy 66 (e.g., RF energy) may be transmitted from the inner surface of the wall of the first vessel 60 and/or ostium 30, into the vessel wall to the ganglia 24 or other renal nerve tissue, and then back into the lumen 63 of the second vessel 62 to the guidewire 54. Thus, such a configuration may direct the electrical energy 66 to the ganglia 24 or other renal nerve tissue while localizing the electrical pathway to the region of the ostium 30, without having to complete an electrical pathway to the exterior of the patient's body. Thus, electrical energy 66 may be focused toward the ganglia 24, or other concentrated area of nerve tissue, to increase the efficiency of the ablation of the nerve tissue. Furthermore, such a configuration may be beneficial in situations where the renal artery 12 is small, short, or abnormal, or in the instance of multiple renal arteries 12, in which case positioning a thermal element of an ablation device directly in the renal artery 12 may be less beneficial, impractical and/or unattainable.

Alternatively, guide wire 54 may remain in first vessel 60 (e.g., guide wire 54 may not be a ground electrode when it remains in first vessel 60) and thermal energy 66 may be emitted from thermal element(s) 58 through target area(s) 68 and perivascular tissue to ablate or modify the perivascular tissue in an electrically unipolar manner.

In addition, the heating of perivascular tissue may include utilizing multiple thermal elements 58 to heat multiple target areas 68 extending through first vessel 60 to the perivascular tissue. Where there are multiple target areas 68, each target area 68 may be heated simultaneously, or each target area 68 may be heated sequentially, or each target area 68 may be heated randomly, or each target area 68 may be heated singularly, or each target area 68 may be heated with a combination of these techniques (e.g., a first set of two target areas 68 may be heated and then a second set of target areas 68 may be heated). Further, each of the target areas 68 may be heated by the same or separate and/or different thermal element 58 positioned in first vessel 60, which may facilitate the various methods of heating multiple target areas 68.

Further, although thermal elements 58 have been described as being electrodes or other elements that heat a tissue through emitting an electrical energy field 66, one or more thermal elements 58 may operate to cool tissue. For example, one or more of thermal elements 58 may comprise Peltier electrodes for cooling target area(s) 68.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method of ablating tissue, comprising:
    inserting an ablation assembly into a first lumen of a body of a patient adjacent a second lumen, the ablation assembly comprising an elongated member having a distal end and a proximal end, and a plurality of thermal elements disposed on the elongate member proximate the distal end;
    positioning a ground electrode within the patient's body;
    expanding the plurality of thermal elements radially away from the elongate member into contact with a wall of the first lumen; and
    directing ablation energy from the plurality of thermal elements toward the ground electrode to ablate tissue between the first and second lumens.

2. The method of claim 1, wherein the thermal elements are expanded into contact with first lumen around a circumference of the lumen wall.

3. The method of claim 1, wherein the thermal elements are arranged around a circumference of an outer surface of an expandable member disposed at the distal end of the elongated member.

4. The method of claim 1, wherein the directing step comprising directing the ablation energy along a localized electrical pathway between the plurality of thermal elements and the ground electrode to ablate tissue between the first and second lumens.

5. The method of claim 1, comprising positioning the ground electrode within the second lumen.

6. The method of claim 1, wherein the directing energy step comprises simultaneously directing ablation energy from the plurality of thermal elements through the tissue between the first and second lumens.

7. The method of claim 1, wherein the directing energy step comprises sequentially directing ablation energy from the plurality of thermal elements through the tissue between the first and second lumens.

8. A method of treating tissue, comprising:
    inserting an energy delivery assembly into a first lumen of a body of a patient adjacent a second lumen, the energy delivery assembly comprising an elongated member having a distal end and a proximal end, and at least one energy delivery element disposed on the elongate member proximate the distal end;
    positioning a ground electrode within the patient's body;
    expanding the at least one energy delivery element radially away from the elongate member into contact with a wall of the first lumen; and
    directing energy along a localized electrical pathway between the at least one energy delivery element and the ground electrode to affect tissue between the first and second lumens without having to complete an electrical pathway to an exterior of the patient's body.

9. The method of claim 8, wherein the ground electrode is coupled to the elongated member.

10. The method of claim 8, further comprising an expandable member disposed at the distal end of the elongated member and the at least one energy delivery element arranged on the expandable member.

11. The method of claim 10, wherein the expandable member is a balloon and the at least one energy delivery element is disposed on the balloon.

12. The method of claim 8, comprising positioning the ground electrode within the second lumen.

13. The method of claim 8, wherein the directing energy step comprises energizing the at least one energy delivery element in a bipolar arrangement with the ground electrode.

14. A method of affecting nerve tissue, comprising:

inserting an RF assembly into a first lumen of a body of a patient adjacent a second lumen, the RF assembly comprising an elongated member having a distal end and a proximal end and at least one energy delivery element disposed on the elongate member proximate the distal end;

positioning a ground electrode within the patient's body;

expanding the at least one energy delivery element radially away from the elongate member into contact with a wall of the first lumen; and directing RF energy along a localized electrical pathway between the at least one energy delivery element and the ground electrode to nerve tissue between the first and second lumens.

15. The method of claim 14, wherein the first and second lumens are vessels.

16. The method of claim 14, wherein the first and second lumens are adjacent vessels and the tissue comprises perivascular nerve tissue.

17. The method of claim 14, wherein the directing RF energy step comprises directing an amount of ablative energy sufficient to alter the nerve tissue.

18. The method of claim 14, wherein the elongated member includes an expandable member at the distal end, the at least one energy delivery element is disposed on an outer surface of the expandable member.

19. The method of claim 18, wherein the expanding step comprises the expandable member moving between a contracted first position to an expanded second position.

20. The method of claim 19, wherein the expandable member is a balloon and the expanding step comprises the balloon inflating from the contracted first position to the expanded second position.

* * * * *